(12) United States Patent
Ritger et al.

(10) Patent No.: US 6,217,560 B1
(45) Date of Patent: Apr. 17, 2001

(54) LUER CONNECTOR

(76) Inventors: Philip L. Ritger, 5821 Raphael Dr., Huntington Beach, CA (US) 92649; Miguel Leon, 14102 High St., Whittier, CA (US) 90605

(*) Notice: Subject to any disclaimer, the term of this patent is extended or adjusted under 35 U.S.C. 154(b) by 0 days.

(21) Appl. No.: 09/168,368

(22) Filed: Oct. 7, 1998

Related U.S. Application Data

(62) Division of application No. 08/587,739, filed on Jan. 19, 1996.

(51) Int. Cl.$^7$ .................................................... A61M 5/00
(52) U.S. Cl. ............................................ 604/243; 264/338
(58) Field of Search .......................... 604/239, 240–243, 604/525; 29/402.18, 436, 459, 506, 521; 264/316, 338

(56) References Cited

U.S. PATENT DOCUMENTS

| | | |
|---|---|---|
| 2,695,613 | 11/1954 | MacGregor . |
| 2,767,710 | 10/1956 | Blackman . |
| 2,828,743 | 4/1958 | Ashkenaz et al. . |
| 2,902,995 | 9/1959 | Loper . |
| 3,150,661 | 9/1964 | Maki . |
| 3,469,581 | 9/1969 | Burke . |
| 3,472,227 | 10/1969 | Burke . |
| 4,040,421 | 8/1977 | Young . |
| 4,096,229 | * 6/1978 | Maivar .................. 264/316 |
| 4,430,080 | * 2/1984 | Pasquini et al. ........ 604/240 |
| 4,589,871 | * 5/1986 | Imbert .................. 604/240 |
| 4,822,343 | 4/1989 | Beiser . |
| 5,017,191 | 5/1991 | Yamada et al. . |
| 5,026,355 | 6/1991 | Sweeney et al. . |
| 5,069,670 | 12/1991 | Vetter et al. . |
| 5,257,832 | 11/1993 | Phan et al. . |
| 5,263,945 | 11/1993 | Byrnes et al. . |
| 5,284,134 | 2/1994 | Vaughn et al. . |
| 5,312,352 | 5/1994 | Leschinsky et al. . |
| 5,312,377 | 5/1994 | Dalton . |
| 5,344,414 | 9/1994 | Lopez et al. . |
| 5,405,339 | 4/1995 | Kohnen et al. . |

FOREIGN PATENT DOCUMENTS

| | | |
|---|---|---|
| 2533594 | 2/1976 | (DE) . |
| 361594 | 11/1931 | (GB) . |

OTHER PUBLICATIONS

International Standard (ISO) 594/1 "Conical fittings with a 6% (Luer) taper for syringes, needles and certain medical equipment"—Part 1: General requirements, Ref. No. ISO 564/1–1986 (E).

International Standard (ISO) 594–2 "Conical fittings with a 6% (Luer) taper for syringes, needles and certain other medical equipment"—Part 2: Lock fittings, Ref. No. ISO 594–2:1991 (E).

* cited by examiner

*Primary Examiner*—Anhtuan T. Nguyen
(74) *Attorney, Agent, or Firm*—Knobbe, Martens, Olson & Bear LLP

(57) ABSTRACT

Disclosed herein is a luer connector which exhibits an improved engagement force, in comparison to a standard luer connector, when a fluid contaminant is present between the contact surfaces of mated luer fitments. The luer connector of the present invention comprises a textured contact surface which is adapted to trap or channel fluid contaminants away from the contact surfaces of mated luer fitments. Also disclosed herein is a method of making a luer connector with a textured contact surface.

6 Claims, 6 Drawing Sheets

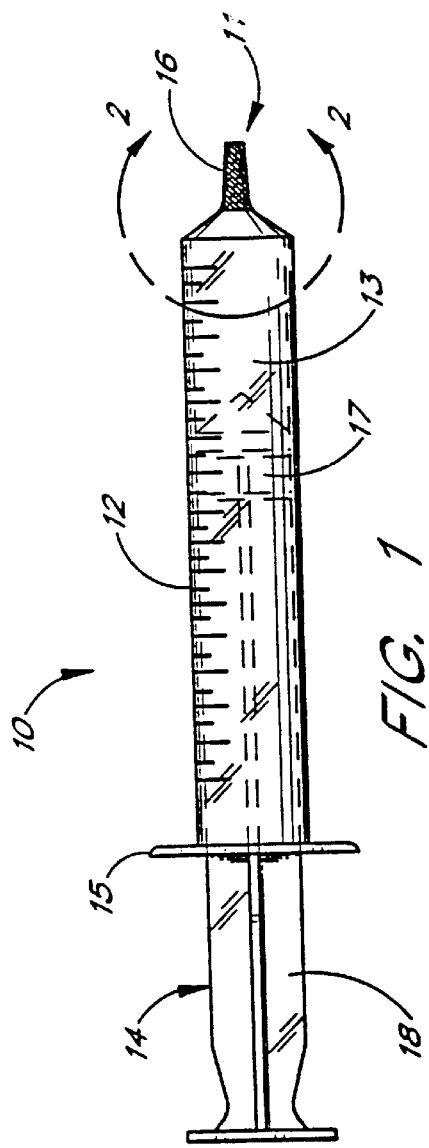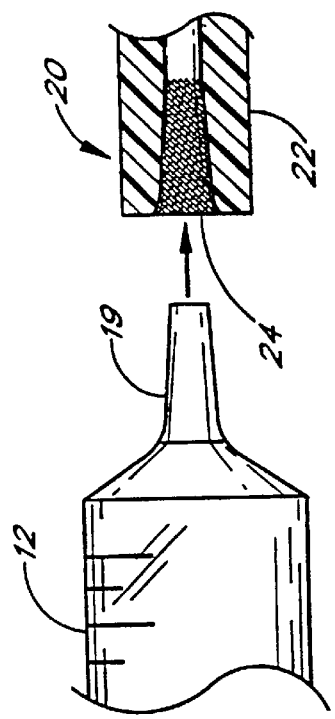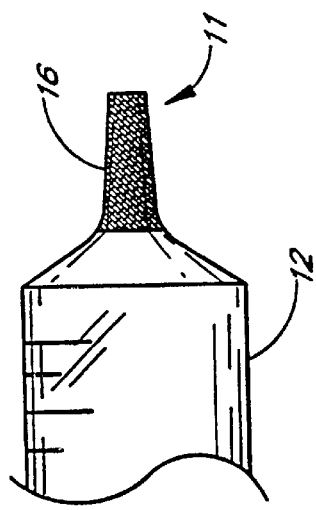

LUER CONNECTOR

This application is a division of Ser. No. 08/587,739 Jan. 19, 1996.

BACKGROUND OF THE INVENTION

The present invention relates to fitments for connecting medical devices, and in particular, to luer fittings having a textured contact surface.

A conventional luer fitting or fitment generally comprises a conically-shaped element which is adapted to form a relatively air-and-liquid tight seal when mated to a complementary fitting, as for example, a syringe tip to a catheter hub. The surface of the luer fitting which contacts the complementary fitting is ordinarily smooth. Such luer fittings are well known in the art, see International Standard Organization (ISO) 594/1-1986, and have been incorporated into a variety of medical devices.

Once connected, it is important that luer fitments do not become accidentally disengaged during a medical procedure. Such accidental disengagement could result in fluid loss or fluid contamination, which in turn, could have adverse consequences for a patient.

Under most circumstances, the frictional fit between conventional mated luer fitments is sufficient to prevent accidental disengagement of the fitments. However, when fluid contaminants or wetting agents are present between the contact surfaces of mated luer fittings, the fluid contaminants tend to act as a lubricant. The lubricating nature of the fluid contaminants diminishes the frictional force, otherwise known as "engagement force", which must be overcome to separate the luer fittings, and thus increases the possibility of accidental disengagement of the fittings.

Various solutions have been proposed in the prior art to overcome the problem of fluid contaminants lubricating luer fittings. For example, ISO 594-2 1991-05-01 teaches luer fittings with interlocking threads and engagement structure. To connect luer fittings of this design, a medical service provider brings the fittings together, and then secures them with a twisting motion. While this may be a practical solution for many applications, it may be undesirable where rapid engagement and disengagement of the luer fittings is preferred.

U.S. Pat. No. 4,589,871 to Imbert teaches applying a coating on the exterior surface of a syringe tip (male luer fitment) to increase the roughness of the tip. It is stated therein that increasing tip roughness in this manner increases the frictional fit of mated luer components, making them harder to separate in comparison to identically sized conventional luer fittings. However, such coating processes may involve costly post-manufacturing application and quality control steps. Furthermore, for certain medical applications, it may be desirable to use a luer connector, which in addition to being resistant to the lubricating effects of fluid contaminants, also has a frictional fit which is substantially the same as identically sized conventional luer fittings.

Thus, there remains a need for a luer fitting resistant to the lubricating effects of fluid contaminants and a method of manufacturing the same. Optimally, such a luer fitting could be manufactured by a low-cost process, avoiding the need for application of coatings or use of abrasive as taught by the prior art. Preferably, such a luer fitting would be produced in a manner so as not to substantially alter the frictional fit of the luer fittings in comparison to conventional luer fittings.

SUMMARY OF THE INVENTION

The present invention is directed to a luer fitting with a textured contact surface, which in comparison to conventional luer fittings, exhibits an improved engagement force when fluid contaminants are present between the contact surfaces of mated luer fitments. Advantageously, luer fittings of the present invention can be manufactured by conventional thermoplastic molding techniques, without the need for subsequent coating processes or use of abrasive.

In accordance with one aspect of the present invention, there is provided a syringe having a hollow barrel with an open end and a conical tip. The conical tip is adapted for insertion into a female fitment with a conical inner surface. A plunger assembly is inserted into the open end, the plunger assembly and the hollow barrel defining an internal chamber for retaining fluid. The exterior surface of the tip is textured, such that the force required to disengage the textured tip from the female fitment when a fluid contaminant is present between the tip and fitment is equal to or greater than the force required to disengage the tip and fitment when the tip and fitment are dry.

In accordance with a second aspect of the present invention, there is provided a method of improving the engagement force of a moistened luer fitment by modifying the surface of the luer fitment. To practice the method, a first luer fitment with a textured surface is provided. Then, the first luer fitment is joined with a second luer fitment having a second surface, such that the textured surface contacts the second surface. Advantageously, the textured surface on the first luer fitment is adapted to direct a fluid contaminant away from the textured and second surfaces, such that the force required to disengage the first luer fitment from the second luer fitment when the fitments are dry is equal to or less than the force required to disengage the first luer fitment from the second luer fitment when a fluid contaminant is present between the first and second fitments.

In accordance with a third aspect of the present invention, there is disclosed a method of modifying the surface of a luer fitment so that the engagement force of the fitment in a moistened state equals or exceeds the engagement force in an unmoistened state. The first step of the method is to provide a mold adapted to form a textured surface on a luer fitment. Then, a luer fitment formed of a material deformable by heat or pressure, or a combination of both, is inserted into the mold. Heat and/or pressure are then applied to the fitment by the mold, such that a textured surface is imprinted on the luer fitment. The luer fitment is then permitted to cool, if necessary, and removed from the mold.

BRIEF DESCRIPTION OF THE DRAWINGS

FIG. 1 is a side view of a syringe having a luer tip with a textured surface in accordance with the present invention.

FIG. 2 is an enlargement of region 2—2 of FIG. 1, further illustrating the textured surface of the luer tip.

FIG. 3 is a cross-sectional schematic view of a female luer fitment having a textured interior surface in accordance with the present invention.

FIG. 4b is a top view of the die of FIG. 4a.

DETAILED DESCRIPTION OF THE PREFERRED EMBODIMENT

Figure 4A:
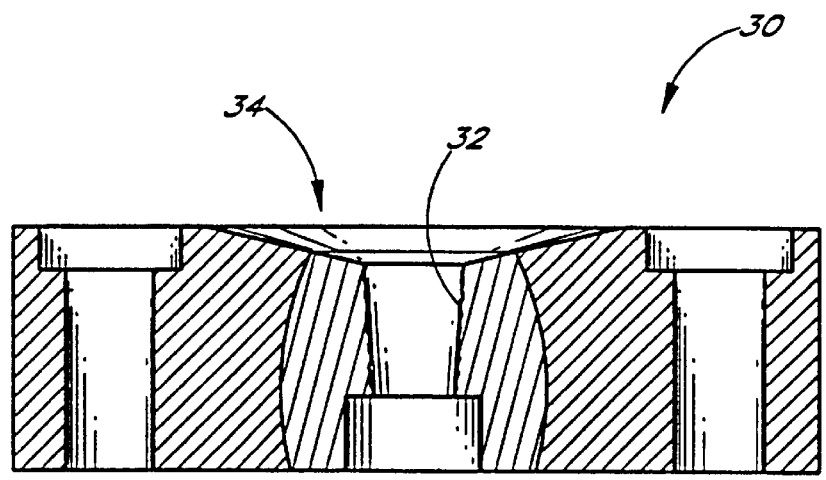
FIG. 4a is a cross-sectional schematic view of a die used to imprint a textured surface onto a male luer fitment.

Referring to FIG. 1, there is depicted a syringe 10 having a luer tip 11 incorporating the surface modifications of the present invention. Although illustrated in the context of a simple syringe, it is to be understood that the fitment surface modifications of the present invention can be readily adapted to a wide variety of medical devices featuring conically shaped fitments. For example, the present inventors contemplate the use of the surface modifications of the present invention in other medical applications featuring luer connectors, such as intravenous drug delivery lines, needle hub attachments, catheter fitments, blood collection fitments and other fluid sampling sites. The manner of adapting the present invention to medical devices having these various functionalities will become readily apparent to those of skill in the art in view of the description which follows.

Syringe 10 generally comprises an elongate hollow barrel 12 which terminates in a tip 11 at its distal end, and has an opening (not shown) and a flange 15 at its proximal end. A plunger assembly 14, comprising a plunger rod 18 and a piston 17, is inserted into the proximal opening in barrel 12. The piston 17 and internal surface of barrel 12 define an internal chamber 13 of varying volume for retaining fluids. Internal chamber 13 is in fluid communication with a passageway extending through tip 11, so that as plunger rod 18 is forced inward into barrel 12, fluids retained within the internal chamber are expelled from syringe 10 through tip 11. Alternately, if plunger rod 18 is withdrawn from barrel 12, fluids will tend to pass proximally through tip 11 through the passageway, and into internal chamber 13. Syringes of this design are well known to those of skill in the art. See for example U.S. Pat. No. 2,767,710 issued to Blackman.

In one preferred embodiment, tip 11 is a conically-shaped luer fitment, as is known to those of skill in the art. In this embodiment, luer tip 11 has a 6% taper from its proximal to its distal end, and other design characteristics, so that it is in compliance with the standards set forth by the International Standard Organization (ISO), such as those present in ISO Ref. No. 594/1-1986(E), the text of which is incorporated herein by reference.

Referring to FIG. 2, there is depicted an enlargement of region 2—2 of FIG. 1, better illustrating the surface modifications to luer tip 11 which are the subject of the present invention. As illustrated in FIG. 2, the exterior surface of tip 11 has been modified to have a textured surface 16, so that tip 11 no longer possess the smooth exterior of conventional luer fitments. The textured surface 16 generally comprises a plurality of small depressions or cavities on the exterior surface of luer tip 11.

Generally, when conventional smooth-surfaced male and female luer fitments are joined, the frictional fit between the contacting surfaces of the two fitments is sufficient to ensure that the fitments stay joined during a variety of typical medical applications. However, when fluid contaminants are present between the contact surfaces of the smooth surfaced fitments, the fluid contaminants tend to act as a lubricant. The lubricating nature of the fluid contaminants generally decreases the force required to disengage the two fitments. This is often undesirable, as it tends to increase the possibility of accidental disengagement.

However, when textured luer tip 11 is mated with a conventional female fitment with a smooth interior surface, the textured surface 16 on luer tip 11 will function to trap or channel any fluid present between the contact surfaces of the two fitments away from the contact surfaces and into the depressions. As a result, even when fluid contaminants are present, a significant portion of each fitment surface is capable of making contact with the opposing fitment, and the lubricating effects of the fluid contaminant are decreased or eliminated. Consequently, in comparison to conventional luer fitments, the textured surface 16 of luer tip 11 results in an improved engagement force when the contact surfaces between two fitments have been contaminated by fluids. For example, it has been found that when a luer fitment of the present invention is used with a conventional second luer fitment, the engagement force of the fitments when contaminated by fluids is substantially the same as, or sometimes slightly greater than, the engagement force on the same fitments when dry.

Furthermore, an important characteristic of the textured surface 16 is that, in comparison to identically dimensioned conventional luer fittings, there is no significant change in the engagement force of dry mated components. In other words, the textured surface of the present invention acts to improve the engagement force of the fluid contaminated fitments without increasing the frictional fit of, or force required to separate, the dry parts, when compared to identically dimensioned conventional luer fitments.

A wide variety of patterns can be used to create textured surface 16 and still achieve the benefits of the present invention. For example, textured surface 16 can take the form of random dimpling, cross-hatching, or radial, circumferential, or horizontal markings. Other patterns which create equivalent depressions or cavities can also be used to provide surface texture 16, as will be appreciated by those of skill in the art.

The limitations on the type of texture pattern which can be used are mainly dictated by the intended use of the fitment. Thus, for example, if the luer fitment must comply with the standards set forth in ISO Ref. 594/1, or other standards, then the texture pattern chosen must not be of such a variety so as to alter the dimensional or functional characteristics of the luer fitment outside of the acceptable range specified by the standard. Similarly, if the luer fitment is intended to provide a sterile barrier, then a pattern of texture should be chosen which avoids the creation of a continuous microbial pathway along the contacting surfaces of the two fitments.

The advantages provided by the textured surface of the present invention are equally applicable to other luer fitments besides syringe tip 11. Accordingly, illustrated in FIG. 3 is a female luer fitment 20, in which conical inner surface 24 has been textured in accordance with the present invention. Also depicted in FIG. 3 is a syringe with a conventional smooth luer tip 19. As discussed previously, textured surface 24 functions to trap or channel away any fluid contaminants present between the contact surfaces of tip 17 and textured surface 24 to the depressions in the textured surface, thereby minimizing or eliminating the adverse lubricating effects of fluid contaminants. Accordingly, in comparison to two mated conventional luer fitments, female fitment 20 and luer tip 17 will exhibit an improved engagement force when fluid contaminants are present at their contact surfaces.

Moreover, the benefits of the present invention are also applicable to a luer fitment assembly wherein both luer fitments have a textured surface. Thus, for example, considering an embodiment featuring a syringe tip and corresponding female fitment, as illustrated in FIGS. 1–3, it is within the scope of the present invention to provide both the male and female fitments with textured surfaces. In such an embodiment, the textured surface on each luer fitment will function to trap or channel fluid contaminants away from the contact surfaces, thereby improving the engagement force of the moistened components, as discussed above.

The advantages of the present invention especially lend themselves to certain type of medical devices, such as a Foley balloon catheter. A Foley balloon catheter is a type of urological drainage catheter used for long term bladder drainage procedures, and is well known in the medical field. The Foley catheter features a female luer fitment with a spring-loaded fluid check valve to control the flow of fluid used to inflate the catheter balloon. Upon insertion of a male luer fitment, such as a syringe tip, into the female fitment, the fluid check valve is forced open and an inflating fluid can be injected. Upon removal of the male luer fitment, the valve closes and prevents the inflating fluid from escaping.

Because the fluid check valve has a spring component, it imparts an axial force on male luer fitments inserted therein. Under most circumstances, the engagement force between mated dry luer fitments is enough to prevent the axial force from separating the two fitments. However, when a fluid contaminant is present between the contact surfaces of a male luer fitment and a Foley catheter female fitment, the lubricating nature of the fluid contaminant may diminish the engagement force to such an extent that the axial force may cause separation of the two fitments. This undesirable result may be avoided through use of the present invention, by providing a textured surface to the male and/or female fitments of the Foley catheter assembly.

Figure 4B:
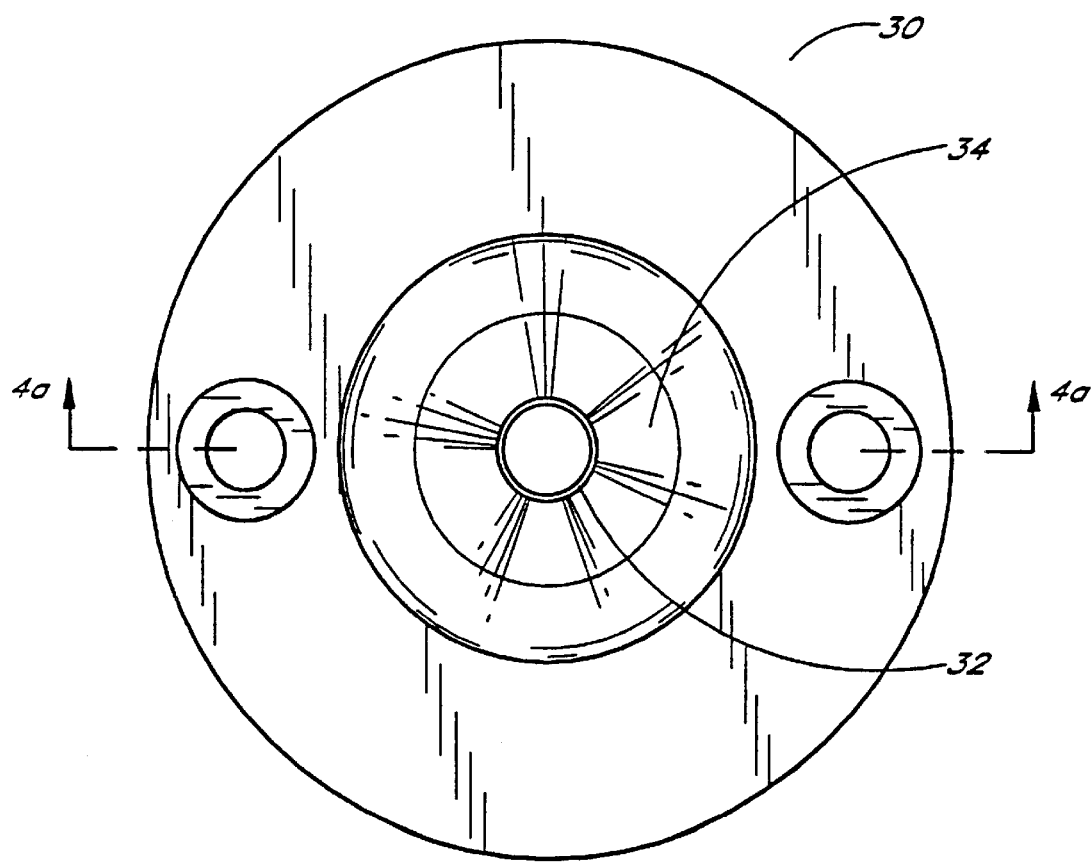

Illustrated in FIGS. 4a and 4b is die 30, which may be used to texture the surface of a syringe tip in accordance with the present invention. As depicted in FIGS. 4a and 4b, die 30 is generally circular in shape. However, as will be appreciated by those of skill in the art, die 30 may take any of a variety of shapes, as for example, rectangular or square.

Die 30 has an access port 34 for introduction of a syringe tip. The interior surface 32 of die 30 which contacts the syringe tip is machined with the surface texture to be imparted to the syringe tip. Die 30 may be manufactured from a variety of materials, such as metals, ceramics, or any other material which is suitable to imprint a texture onto the surface of a deformable syringe tip.

Figure 5:
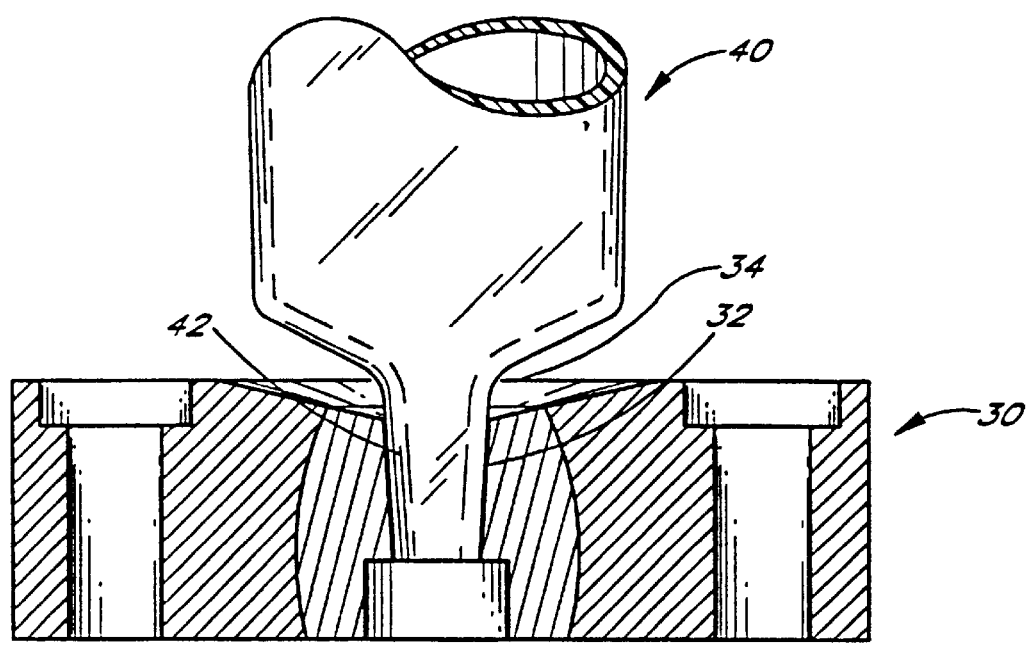
FIG. 5 is a cross-sectional schematic view of a syringe tip inserted into the texture imprinting die.

Referring to FIG. 5, there is illustrated a syringe 40 having a conventional smooth luer tip 42 inserted into die 30 for imprinting of a textured surface. Syringe 40 may be made of any material which may be deformed as a result of heat or pressure, or a combination thereof. In one preferred embodiment, syringe 40 is first manufactured of a thermoplastic material by conventional means known to those of skill in the art. Examples of thermoplastic materials suitable to practice the present invention include polyethylene, polypropylene, polyvinyl chloride (PVC), polystyrene, polycarbonate, polyester or other various copolymer formulations related to these generic material types.

Syringe 40 is then inserted into die 30 as part of a post-manufacturing step, so that luer tip 42 contacts the machined surface 32 of die 30. Heat and/or pressure are then applied to tip 42 by die 30, such that the thermoplastic material of tip 42 deforms and the textured pattern of machined surface 32 is imprinted on luer tip 42 to create a textured surface. Syringe 40 is then removed from die 30, and if heating was involved, allowed to cool.

As will be appreciated by those of skill in the art, the precise parameters for the amount of heat and/or pressure which must be applied to impart the textured surface will be dictated by the materials of the fitment. For thermoplastic materials such as polypropylene, die 30 will generally be heated to a temperature ranging from about 60 to 140 degrees Centigrade, more preferably from about 80 to 120 degrees, to facilitate deformation of the luer fitment. Forces ranging from about 5 to 30 lbs., more preferably 10 to 20 lbs., may also be applied to polypropylene fitments as part of the process used to create the surface texture. It will be clear to those of skill in the art, however, that a particular heat and/or pressure value for texturing might fall outside the quoted ranges, and still be effective, depending upon the luer fitment material and desired characteristics.

Figure 6:
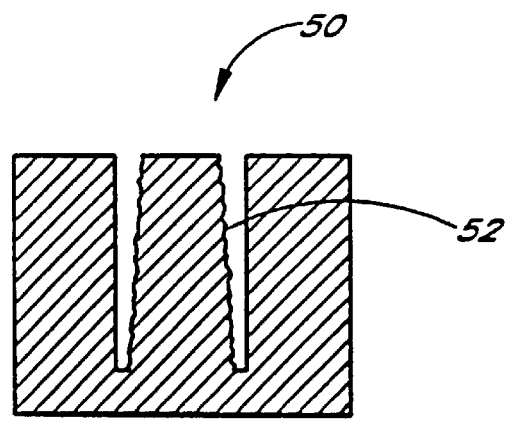
FIG. 6 is a cross-sectional schematic view of a die which may be used to imprint a textured surface on a female luer fitment.

Depicted in FIG. 6 is a cross-sectional view of a die 50 which may be used to impart a texture to the surface of a female fitment. Die 50 is adapted to receive a preformed conically shaped female luer fitment. The interior surface 52 of die 50 is machined with the surface texture to be imparted to the female fitment. In other respects, the manner of using die 50 to impart a surface texture to a luer fitment is identical to that described above for a male luer fitment (i.e., syringe tip).

Alternately, the textured surface of the present invention can be imparted to a luer fitment by any of a variety of other means known to those of skill in the art. For example, the texture may be imparted as part of the primary manufacturing step, by the use of a mold having a textured surface about the region where the contact surface of the luer fitment is formed. Alternately, surface texture may be applied by the direct application of chemical or mechanical surface etching processes, or by particle blasting with frozen gasses such as carbon dioxide.

EXAMPLE

A textured surface imprinting die, similar to that depicted in FIGS. 4a and 4b, was fabricated from 420 stainless steel. An electro discharge machine (EDM) was used to machine the die about the area where the die contacts the luer fitment to impart surface texture to the fitment. The EDM machine parameters were set to achieve a roughness average of between 4 and 50 micrometers. The lay of the machined surface created by this treatment is best described as non-directional or protuberant.

A conventional male luer fitting, consisting of the tip of a standard 10 cc syringe, manufactured by Becton Dickinson, was modified in accordance with the present invention using the above-described die. The die was heated to between 80 and 120 degrees Centigrade, and the syringe tip was inserted into the die. An axial compressive force, in the range of 10–20 lbs. was then applied to the assembly to engage the luer fitment surface to the die. The combination of heat and pressure resulted in the machined surface of the die being imprinted on the exterior surface of the syringe tip.

The texture imparted to the surface of the luer fitment had a surface roughness of between 0.2 and 4 micrometers. The lay of the textured surface of the syringe tips may be described as non-directional, ground, or blanchard. Syringe tips treated in this manner are referred to as "Improved Luer Tip" in FIGS. 7–9.

Figure 7:
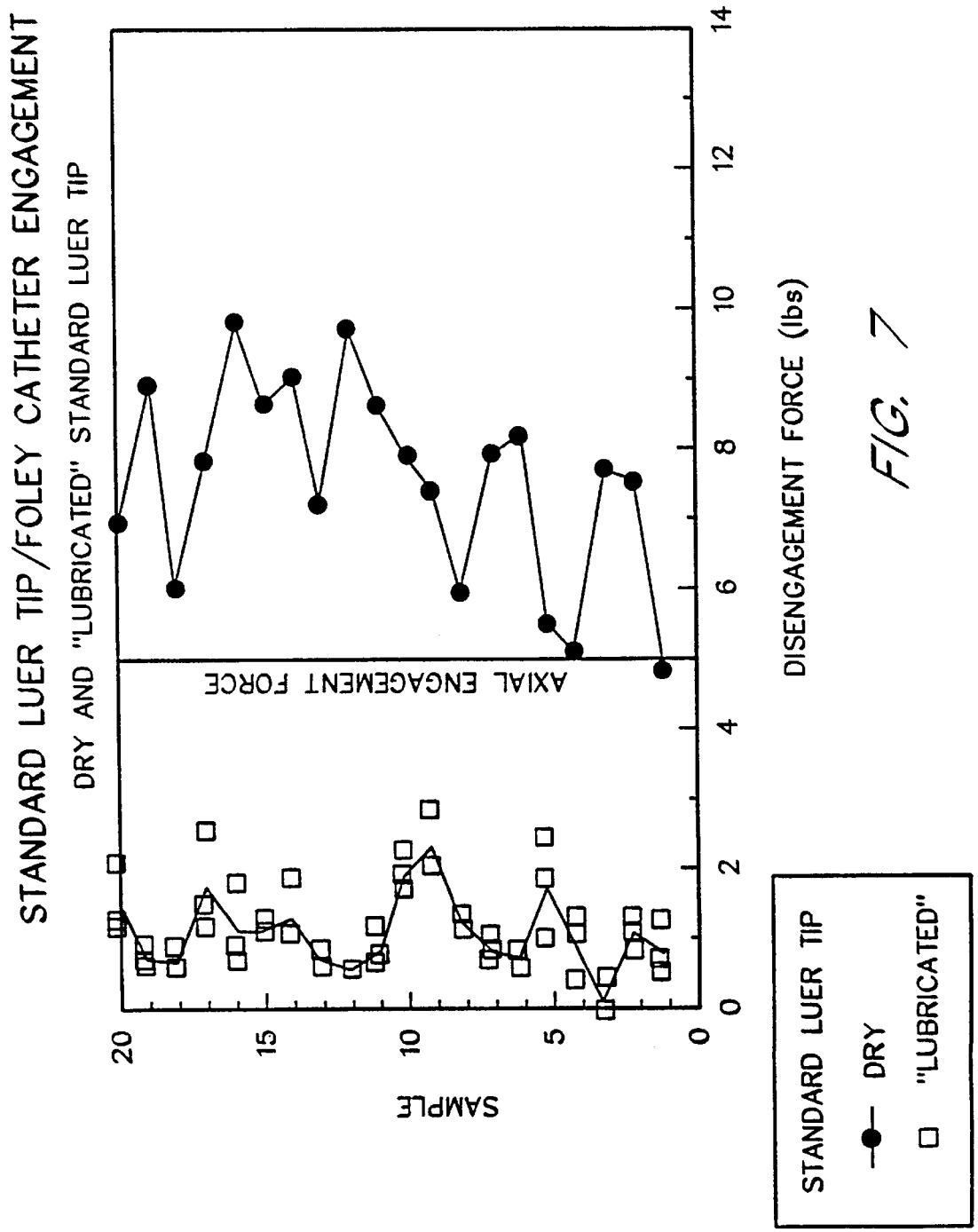
FIG. 7 is a graph illustrating the disengagement force of dry and lubricated conventional (standard) smooth surface luer fitments.
Figure 8:
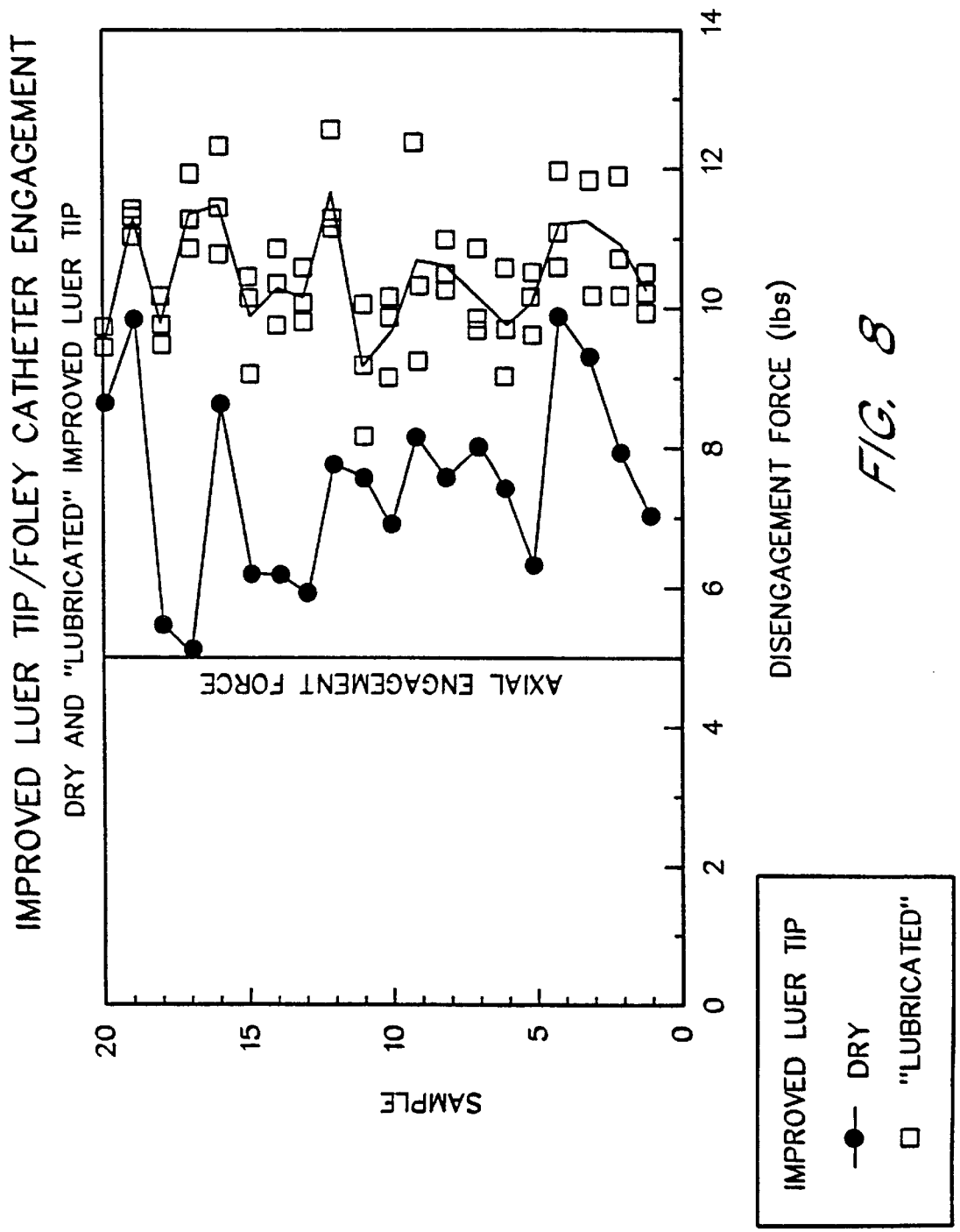
FIG. 8 is a graph illustrating the disengagement force of dry and lubricated luer fitments of the present invention.
Figure 9:
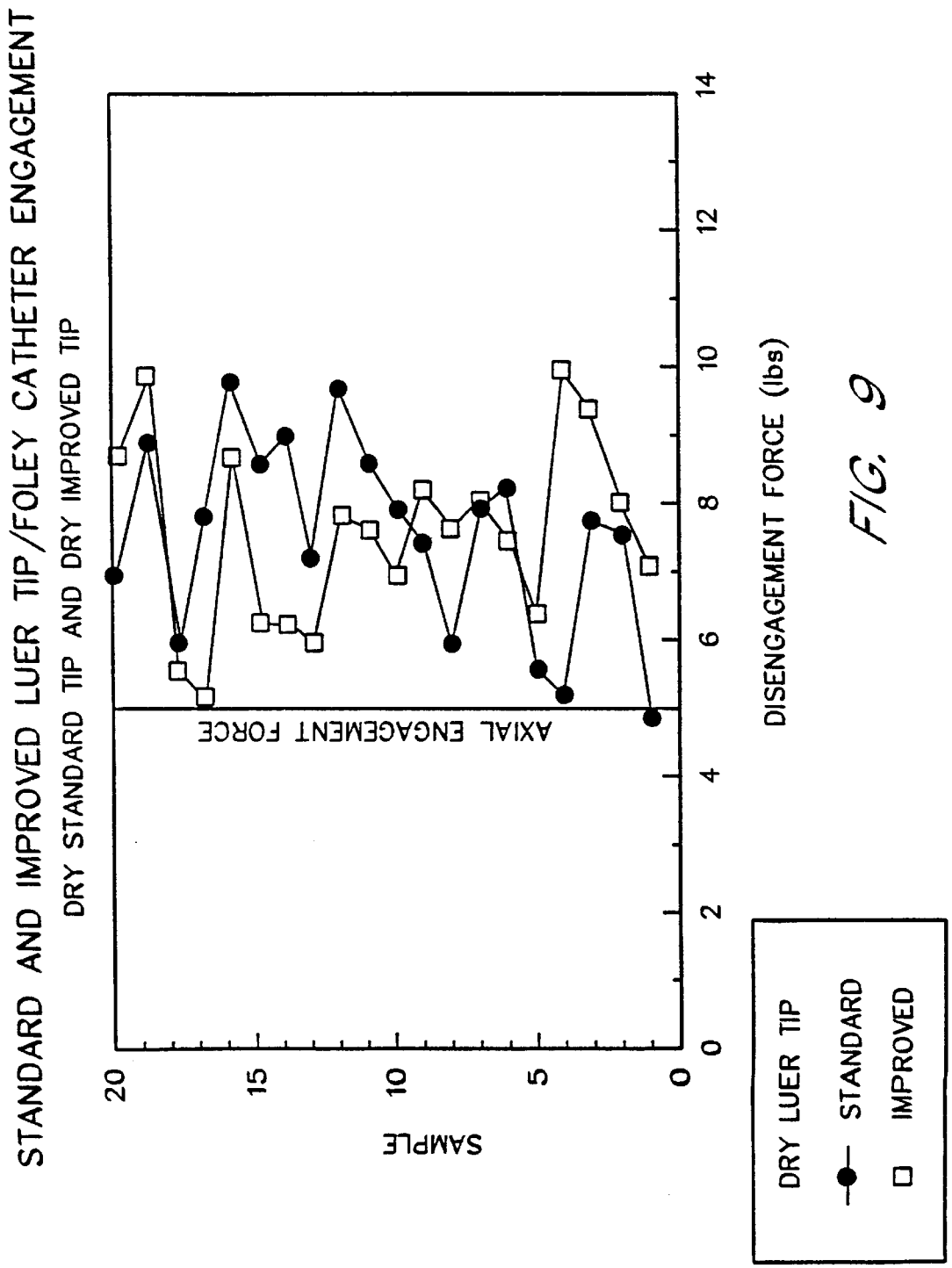
FIG. 9 is a graph illustrating the disengagement force of dry conventional (standard) luer fitments and the textured luer fitment of the present invention.

As a control, an identical unmodified luer connector, referred to as "Standard Luer Tip" in FIGS. 7–9, was used. The female fitting employed in all tests was an industry standard Foley catheter valve, manufactured by C. R. Bard.

The force which must be applied to separate the fitments, thereby overcoming the engagement force of mated luer fittings, is designated as the disengagement force in FIGS.

7–9. As measured, the disengagement force correlates directly with the engagement force of the connected fittings. Thus, a higher disengagement force indicates a higher engagement force of the connected fittings, and conversely, a lower disengagement force indicates a lower engagement force.

The male luer tip to be tested, in either a dry or lubricated state, was inserted into a dry female fitment by applying an axial force of 5 lbs. while twisting to give a rotation not exceeding ninety degrees. The assembled luer fitments were then placed in a retaining fixture of a Tensile/Compression tester, such as those manufactured by Instron.

A separation force was then applied to the luer assembly at a rate of 1–2 inches per minute. The maximum force required to separate the assembly was recorded, and appears in FIGS. 7–9.

The experimental data collected is shown in FIGS. 7–9 without averaging. For each test grouping, twenty syringes were used. The y-axis of each Figure represents the sample number of the syringe. For unmoistened or "dry" tests, a single measurement was made per sample. For the moistened or "lubricated" tests, three consecutive measurements were made per sample for a total of sixty measurements.

Referring to FIG. 7, there is depicted the results of the above-described tests when performed on dry Standard Luer Tips, and Standard Luer Tips moistened (i.e., lubricated) with a fluid contaminant consisting of SteriLub™ Lubrication Gel, manufactured by Horizon Medical, Santa Ana, Calif. As can be seen from the data disclosed in FIG. 7, the moistened Standard Luer Tips have a greatly diminished disengagement force in comparison to the dry Standard Luer Tip.

Referring to FIG. 8, there is depicted the results of the above-described tests when performed on dry and SteriLub™ Lubrication Gel moistened Improved Luer Tips of the present invention. As shown in FIG. 8, the disengagement force of the moistened Improved Luer Tip was, on average, greater than the disengagement force of the dry Improved Luer Tip. Thus, a male luer tip modified in accordance with the present invention functioned to improve the engagement force of mated luer fitments contaminated with a fluid, in comparison to an identically dimensioned standard luer fitment.

Referring to FIG. 9, there is shown the results of the above-described tests when performed on dry Standard Luer Tips and dry Improved Luer Tips of the present invention. As can be seen from FIG. 9, the disengagement force of the Standard and Improved Luer fitments in the dry state is approximately the same. This indicates that the surface texture of the present invention functions to improve the engagement force of the moistened fitments without affecting the frictional fit of the dry components. Thus, in the dry state, the force required to separate a luer fitting of the present invention from a conventional complementary fitting is substantially the same as the force required to separate two identically dimensioned conventional luer fittings.

It will be appreciated that certain variations of the present invention may suggest themselves to those skilled in the art. The foregoing detailed description is to be clearly understood as given by way of illustration, the spirit and scope of this invention being limited solely by the appended claims.

What is claimed is:

1. A method of improving the engagement force of a luer fitment which has been moistened with a fluid contaminant, comprising the steps of:

providing a first luer fitment with a non-coated textured surface;

joining the first luer fitment with a second luer fitment having a second surface, such that the textured surface contacts the second surface;

wherein the textured surface on the first luer fitment is adapted to direct a fluid contaminant away from the textured and second surfaces, such that the force required to disengage the first luer fitment from the second luer fitment when the fitments are dry is substantially the same or less than the force required to disengage the first luer fitment from the second luer fitment when a fluid contaminant is present between the textured and second surfaces.

2. The method of claim 1, wherein the first luer fitment is a syringe tip and the second luer fitment is a complementary female fitment.

3. The method of claim 2, wherein the second luer fitment is a catheter hub.

4. The method of claim 1, wherein the first luer fitment is a female fitment, and the second fitment is a syringe tip.

5. A method of modifying the surface of a luer fitment so that the engagement force of the fitment in a moistened state equals or exceeds the engagement force in an unmoistened state, comprising the steps of:

providing a mold adapted to form a textured surface comprising depressions on a luer fitment;

inserting a luer fitment into the mold, wherein said luer fitment is formed of a material deformable by heat and/or pressure;

applying heat and/or pressure to the fitment by the mold, such that the textured surface comprising depressions is imprinted on the luer fitment; and removing the luer fitment from the mold.

6. The method of claim 5, wherein the luer fitment is formed of a thermoplastic material.

\* \* \* \* \*